United States Patent
Serban et al.

(10) Patent No.: US 10,682,628 B2
(45) Date of Patent: *Jun. 16, 2020

(54) PROCESSES FOR REGENERATING A CATALYST FOR THE SELECTIVE CONVERSION OF HYDROCARBONS

(71) Applicant: UOP LLC, Des Plaines, IL (US)

(72) Inventors: Manuela Serban, Glenview, IL (US); Matthew C. Cole, Evanston, IL (US); Ellen Arnold, Prospect Heights, IL (US); Guanghui Zhu, Arlington Heights, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/177,840

(22) Filed: Nov. 1, 2018

(65) Prior Publication Data

US 2019/0126256 A1 May 2, 2019

Related U.S. Application Data

(60) Provisional application No. 62/580,794, filed on Nov. 2, 2017.

(51) Int. Cl.

| B01J 23/62 | (2006.01) |
|---|---|
| B01J 21/04 | (2006.01) |
| B01J 35/08 | (2006.01) |
| B01J 35/00 | (2006.01) |
| B01J 35/10 | (2006.01) |
| C07C 5/333 | (2006.01) |
| B01J 23/96 | (2006.01) |
| B01J 38/02 | (2006.01) |

(52) U.S. Cl.
CPC ............ *B01J 23/626* (2013.01); *B01J 21/04* (2013.01); *B01J 23/62* (2013.01); *B01J 23/624* (2013.01); *B01J 23/628* (2013.01); *B01J 23/96* (2013.01); *B01J 35/0026* (2013.01); *B01J 35/08* (2013.01); *B01J 35/109* (2013.01); *B01J 35/1061* (2013.01); *B01J 35/1085* (2013.01); *B01J 38/02* (2013.01); *C07C 5/3337* (2013.01); *C07C 2521/04* (2013.01); *C07C 2523/04* (2013.01); *C07C 2523/42* (2013.01); *C07C 2523/58* (2013.01); *C07C 2523/62* (2013.01)

(58) Field of Classification Search
CPC . B01J 23/62; B01J 23/626; B01J 21/04; B01J 23/96; B01J 35/0026; B01J 35/109; B01J 38/02; C07C 5/3337; C07C 2521/04; C07C 2523/58; C07C 2523/62
USPC .......................................................... 502/56
See application file for complete search history.

(56) References Cited

U.S. PATENT DOCUMENTS

| 3,670,044 | A | 6/1972 | Drehman |
|---|---|---|---|
| 4,418,237 | A | 11/1983 | Imai |
| 4,613,715 | A | 9/1986 | Haskell |
| 4,788,371 | A | 11/1988 | Imai et al. |
| 4,914,075 | A | 4/1990 | Bricker et al. |
| 6,756,340 | B2 | 6/2004 | Voskoboynikov et al. |
| 8,309,782 | B2 | 11/2012 | Le Peltier et al. |
| 2005/0033101 | A1 | 2/2005 | Voskoboynikov et al. |
| 2015/0111720 | A1 | 4/2015 | Vaidya et al. |
| 2019/0126256 | A1* | 5/2019 | Serban .................. B01J 23/626 |

FOREIGN PATENT DOCUMENTS

| CN | 1201715 | 12/1998 |
|---|---|---|
| CN | 105214657 | 1/2016 |
| WO | 2015084041 | 6/2015 |
| WO | 2016005896 | 1/2016 |

* cited by examiner

*Primary Examiner* — Edward M Johnson

(57) ABSTRACT

A catalyst for a selective conversion of hydrocarbons. The catalyst includes a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof. The catalyst is a support formed as a spherical catalyst particle with a median diameter between 1.6 mm and 2.5 mm and an apparent bulk density between 0.6 and 0.3 g/cc. Also a process of using such a catalyst for a selective hydrocarbon conversion reaction and a process for regenerating such a catalyst by removing coke from same.

20 Claims, 4 Drawing Sheets

PROCESSES FOR REGENERATING A CATALYST FOR THE SELECTIVE CONVERSION OF HYDROCARBONS

RELATED APPLICATIONS

This application claims priority to U.S. Provisional Patent Application Ser. No. 62/580,794 filed Nov. 2, 2017, the entirety of which is hereby incorporated by reference.

FIELD OF THE INVENTION

This invention relates generally to a new catalytic material, a process for the selective conversion of hydrocarbon using the new catalytic material, as well as a process for regenerating the new catalytic material.

BACKGROUND OF THE INVENTION

Petroleum refining and petrochemical processes frequently involve the selective conversion of hydrocarbons with a catalyst. For example, the dehydrogenation of hydrocarbons is an important commercial process because of the great demand for dehydrogenated hydrocarbons for the manufacture of various chemical products such as detergents, high octane gasolines, pharmaceutical products, plastics, synthetic rubbers, and other products well known to those skilled in the art. One example of this process is dehydrogenating isobutane to produce isobutylene which can be polymerized to provide tackifying agents for adhesives, viscosity-index additives for motor oils, impact-resistant and anti-oxidant additives for plastics and a component for oligomerized gasoline.

The prior art is cognizant of various catalytic composites which contain a Group VIII noble metal component, an alkali or alkaline earth metal component, and a component selected from the group consisting of tin, germanium, lead, indium, gallium, thallium, or mixtures thereof. U.S. Pat. Pub. No. 2005/0033101 and U.S. Pat. No. 6,756,340, both assigned to the present application and the entirety of both which are incorporated herein by reference, describe various catalysts that are useful, efficient, and effective for the selective conversion of hydrocarbons.

However, there remains an ongoing and continuous need for new catalytic material for selective hydrocarbon conversion processes, especially those that improve on one or more characteristics of the known catalytic compositions.

SUMMARY OF THE INVENTION

The present invention provides a new catalytic material, a process for the selective conversion of hydrocarbon using the new catalytic material, as well as a process for regenerating the new catalytic material.

Therefore, the present invention may be characterized, in at least one aspect, as providing a catalyst for a selective conversion of hydrocarbons comprising: a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof; and a support forming a spherical catalyst particle with a median diameter between 1.6 mm and 2.5 mm and an apparent bulk density between 0.6 and 0.3 g/cc.

In at least one other aspect, the present invention may be characterized as providing a process for the selective conversion of hydrocarbons comprising: contacting a hydrocarbon at selective conversion conditions with a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a spherical catalyst particle with a median diameter between 1.6 mm and 2.5 mm and an apparent bulk density between 0.6 and 0.3 g/cc.

In at least another aspect, the present invention may be characterized as providing a process for regenerating a catalyst used for a selective conversion of hydrocarbons comprising: removing coke from a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a spherical catalyst particle with a median diameter between 1.6 mm and 2.5 mm and an apparent bulk density between 0.6 and 0.3 g/cc.

In yet another aspect, the present invention may be broadly characterized as providing a catalyst for a selective conversion of hydrocarbons, the catalyst comprising: a first component selected from the group consisting of Group VIII noble metals and mixtures thereof; a second component selected from the group consisting of alkali metals or alkaline-earth metals and mixtures thereof, and a third component selected from the group consisting of tin, germanium, lead, indium, gallium, thallium and mixtures thereof; and a support forming a catalyst particle, the catalyst particle comprising a plurality of pores, a median diameter between 1.6 mm and 2.5 mm, and an apparent bulk density between 0.6 and 0.3 g/cc, wherein the catalyst particle has an effective carbon dioxide diffusivity at 10° C. of at least $1.6 \times 10^{-6}$ m$^2$/sec, or has an oxygen effective diffusivity at 480° C. of at least $1.5 \times 10^{-7}$ m$^2$/s, or has both.

In still another aspect, the present invention may be broadly characterized as providing a process for the selective conversion of hydrocarbons by: contacting a hydrocarbon at selective conversion conditions with a catalytic composite comprising a first component selected from the group consisting of Group VIII noble metals and mixtures thereof, a second component selected from the group consisting of alkali metals or alkaline-earth metals and mixtures thereof, a third component selected from the group consisting of tin, germanium, lead, indium, gallium, thallium and mixtures thereof, and a support forming a catalyst particle, the catalyst particle comprising a first plurality of pores, a median diameter between 1.6 mm and 2.5 mm, and an apparent bulk density between 0.6 and 0.3 g/cc, wherein the catalyst particle has an effective carbon dioxide diffusivity at 10° C. of at least $1.6 \times 10^{-6}$ m$^2$/sec, or has an oxygen effective diffusivity at 480° C. of at least $1.5 \times 10^{-7}$ m$^2$/s, or has both.

In a further aspect, the present invention may be broadly characterized as providing a process for reducing a time associated with regenerating a catalyst used for a selective conversion of hydrocarbons by: removing coke from a catalyst comprising a first component selected from the group consisting of Group VIII noble metals and mixtures thereof, a second component selected from the group consisting of alkali metals or alkaline-earth metals and mixtures thereof, a third component selected from the group consisting of tin, germanium, lead, indium, gallium, thallium and mixtures thereof, and wherein the time associated with regenerating the catalyst is reduced at least 10% compared to a theoretical time for regenerating the catalyst by the catalyst further comprising a support forming a catalyst particle with a median diameter between 1.6 mm and 2.5 mm and an apparent bulk density between 0.6 and 0.3 g/cc.

In another further aspect, the present invention may be broadly characterized as providing a process for regenerating a catalyst used for a selective conversion of hydrocarbons by: removing coke from a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a catalyst particle with a median diameter between 1.6 mm and 2.5 mm and an apparent bulk density between 0.6 and 0.3 g/cc, and wherein a time associated with removing coke from the catalytic composite is lower than a calculated time to remove coke from the catalytic composite.

In still yet another aspect, the present invention may be broadly characterized as providing a system comprising: at least one processor; at least one memory storing computer-executable instructions; and at least one receiver configured to receive data of an apparatus or stream of a process for the conversion of hydrocarbons, an apparatus or stream in fluid communication with and upstream to the conversion of hydrocarbons, an apparatus or stream in fluid communication with and downstream from the conversion of hydrocarbons, or any combination thereof, where the process for the conversion of hydrocarbons comprises a catalytic composite comprising a first component selected from the group consisting of Group VIII noble metals and mixtures thereof, a second component selected from the group consisting of alkali metals or alkaline-earth metals and mixtures thereof, a third component selected from the group consisting of tin, germanium, lead, indium, gallium, thallium and mixtures thereof, and a support forming a catalyst particle, the catalyst particle comprising a plurality of pores, a median diameter between 1.6 mm and 2.5 mm, an apparent bulk density between 0.6 and 0.3 g/cc, wherein the catalyst particle has an effective carbon dioxide diffusivity at 10° C. of at least $1.6 \times 10^{-6}$ m$^2$/sec, or has an oxygen effective diffusivity at 480° C. of at least $1.5 \times 10^{-7}$ m$^2$/s, or has both.

In another further aspect, the present invention may be broadly characterized as providing a method for receiving data of a process for the selective conversion of hydrocarbons, the method comprising receiving data from at least one sensor of a process comprising: contacting a hydrocarbon at selective conversion conditions with a catalytic composite comprising a first component selected from the group consisting of Group VIII noble metals and mixtures thereof, a second component selected from the group consisting of alkali metals or alkaline-earth metals and mixtures thereof, a third component selected from the group consisting of tin, germanium, lead, indium, gallium, thallium and mixtures thereof, and a support forming a catalyst particle, the catalyst particle comprising a plurality of pores, a median diameter between 1.6 mm and 2.5 mm, and an apparent bulk density between 0.6 and 0.3 g/cc, wherein the catalyst particle has an effective carbon dioxide diffusivity at 10° C. of at least $1.6 \times 10^{-6}$ m$^2$/sec, or has an oxygen effective diffusivity at 480° C. of at least $1.5 \times 10^{-7}$ m$^2$/s, or has both.

Additional aspects, embodiments, and details of the invention, all of which may be combinable in any manner, are set forth in the following detailed description of the invention.

DETAILED DESCRIPTION OF THE DRAWINGS

One or more exemplary embodiments of the present invention will be described below in conjunction with the following drawing figures, in which.

DETAILED DESCRIPTION OF THE INVENTION

Figure 1:
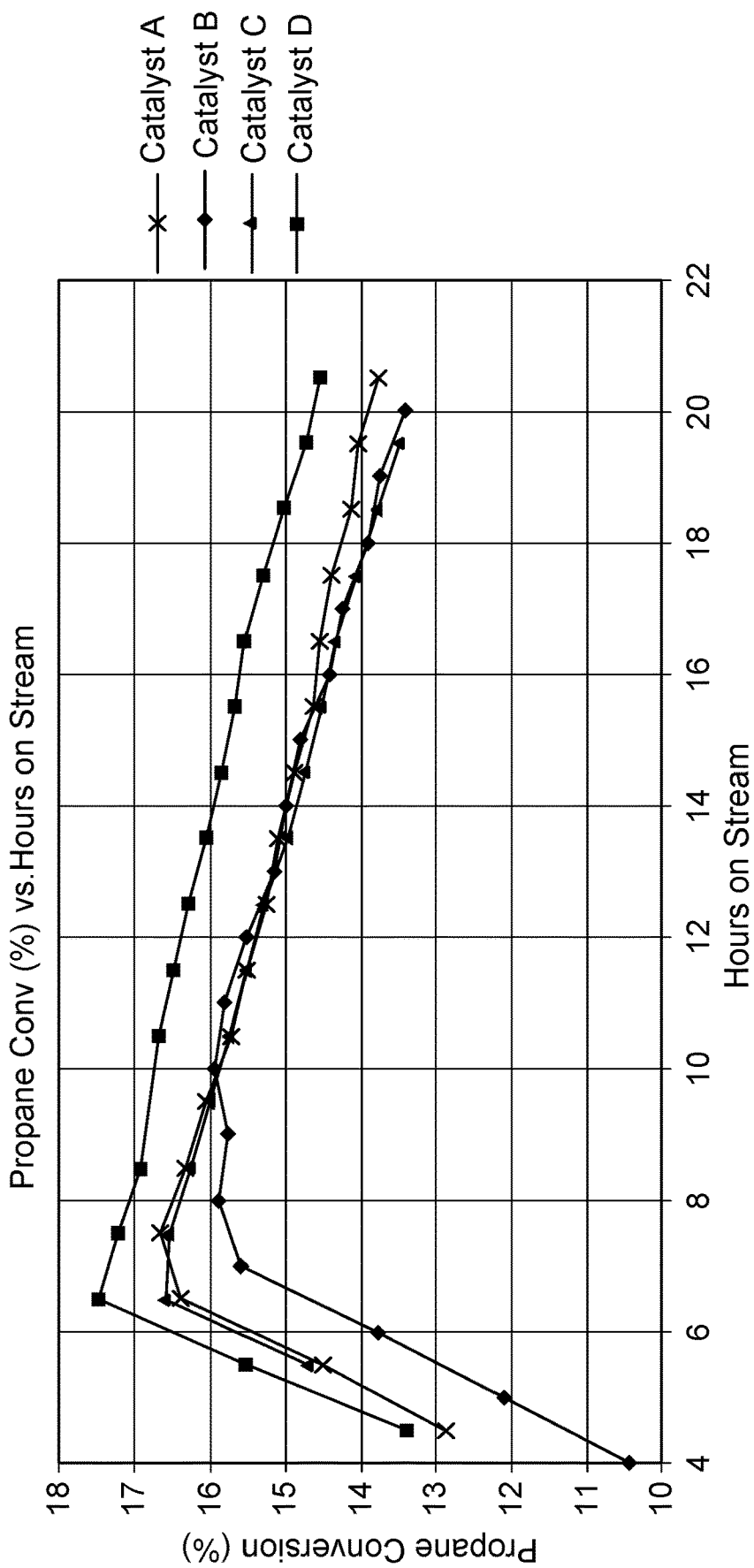
FIG. 1 shows a graph plotting propane conversion versus total hours on stream for a catalyst according to the present invention compared with three prior art catalysts.

As mentioned above, a new catalytic material, a process for the selective conversion of hydrocarbon using the new catalytic material, as well as a process for regenerating the new catalytic material have been invented. The new catalytic material includes low density support material with large pore volume, large porosity, and large pore diameter. The lower density offers several advantages, especially in a diffusion limited reaction. Specifically, this combination of properties provides the new catalytic material with the support high effective diffusivity which leads to improved performance and regeneration (i.e., coke burn) benefits. Additionally, the new catalytic material has higher piece crush strength, potentially leading to less fines produced in the reactor. In addition, the new catalytic material offers the possibility of increasing the throughput for the reactor. This is believed to allow for a higher mass flow through the unit. Additionally, the bed delta pressure is lower for the new catalytic material, allowing for an extended run length in between screen cleanings (longer time until the pressure builds up to the same level as in a smaller pill catalyst bed).

Apart from the advantages associated with the use of the new catalytic composition for the selective conversion of hydrocarbons, the new composition also provides superior and unexpected results associated with regeneration of the spent catalyst. The calculated predicted burn rate differences between current catalysts, and the new catalyst material, taking into account the different diameters, suggest that for the new catalyst material it should take 27% longer for the carbon to burn compared to conventional catalysts. However, even though the new catalyst material is larger, the new catalytic material of this invention had the shortest coke burn time and highest effective diffusivities despite the large pill diameter and long diffusion paths compared to conventional catalysts because of the lower density and consequently the improved porosity, pore volume, pore diameter.

With these general principles in mind, one or more embodiments of the present invention will be described with the understanding that the following description is not intended to be limiting.

As mentioned above, an essential feature of the present invention lies in the characteristics of the support for the instant catalyst. Specifically, according to various aspects of the present invention, it is important that the support have a median diameter between 1.6 mm and 2.5 mm and an apparent bulk density (ABD) between 0.6 and 0.3 g/cc. The median diameter is preferably between 1.8 and 2.2 mm, and most preferably 1.8 mm. The ABD is less than 0.6, preferably between 0.6 to 0.5 g/cc, most preferably between 0.57 and 0.52 g/cc. Additionally, and/or alternatively, it is important for the support to have an average pore diameter between 200 to 350 Angstroms, a porosity of at least 75%, and an ABD between 0.60 and 0.3 g/cc. The ABD may further be between 0.6 and 0.5 g/cc, preferably between 0.57 to 0.52 g/cc, for example the ABD may be 0.57 g/cc. The average pore diameter may further between 240 to 300, or 240 to 280, Angstroms, including any smaller range within these values. Further, the porosity may be between 75% and 85% and may be any value therebetween, or a range made from valves selected between any of the ranges, for example at least 80%. In either embodiment, the lower density support offers advantages when used in a diffusion limited reaction—such as the dehydrogenation of propane—in comparison to similar dehydrogenation catalysts of the prior art. Additionally, a catalyst with the lower density support has surprisingly shown improved coke burn benefits.

The median diameter of the particles was measured via the Dynamic Image Analysis using a CAMSIZER®. Two cameras capture a continuous series of images of particles as they pass in front of an LED panel. The images are processed in real-time using the size and shape parameters defined in the software.

In order to measure the ABD, the substance is put into a receiver of known dimensions and weight. The International Standard ISO 697 distinguishes two types for the determination of apparent bulk density. The basically differ in the size of the receivers used. The instruments for the determination of apparent density imply a lockable funnel of fixed dimensions, a receiver and a stand that holds them together in a defined position. The funnel is then filled with the sample of powder or granule then opened. The sample then flows into the receiver with the known volume and the apparent density is obtained by weighing the receiver.

The porosity, the pore diameters, and the total intrusion volumes were measured using method UOP 578-11 Automated Pore Size Distribution of Porous Substances by Mercury Porosimetry. The volume change in a mercury column was monitored while being subjected to a constant applied pressure from sub ambient to 60,000 psi. The measurement was conducted in both intrusion and extrusion modes.

Returning to the catalytic materials of the present invention, the support comprises a number of catalytic components including a Group VIII noble metal component, an alkali or alkaline earth component, and a component selected from the group consisting of tin, germanium, lead, indium, gallium, thallium, or mixtures thereof.

The Group VIII noble metal may be selected from the group consisting of platinum, palladium, iridium, rhodium, osmium, ruthenium, or mixtures thereof. Platinum, however, is the preferred Group VIII noble metal component. Preferably the Group VIII noble metal component is well dispersed throughout the catalyst. It generally will comprise about 0.01 to 5 wt. %, calculated on an elemental basis, of the final catalytic composite. Preferably, the catalyst comprises about 0.1 to 2.0 wt. % Group VIII noble metal component, especially about 0.1 to about 2.0 wt. % platinum.

The Group VIII noble metal component may be incorporated in the catalytic composite in any suitable manner such as, for example, by coprecipitation or cogelation, ion exchange or impregnation, or deposition from a vapor phase or from an atomic source or by like procedures either before, while, or after other catalytic components are incorporated. The preferred method of incorporating the Group VIII noble metal component is to impregnate the alumina support with a solution or suspension of a decomposable compound of a Group VIII noble metal. For example, platinum may be added to the support by commingling the latter with an aqueous solution of chloroplatinic acid. Another acid, for example, nitric acid or other optional components, may be added to the impregnating solution to further assist in evenly dispersing or fixing the Group VIII noble metal component in the final catalyst composite.

The alkali or alkaline earth component of the present invention may be selected from the group consisting of cesium, rubidium, potassium, sodium, and lithium or from the group consisting of barium, strontium, calcium, and magnesium or mixtures of metals from either or both of these groups. Potassium is the preferred second catalytic component. It is believed that the alkali and alkaline earth component exists in the final catalytic composite in an oxidation state above that of the elemental metal. The alkali and alkaline earth component may be present as a compound such as the oxide, for example, or combined with the carrier material or with the other catalytic components. Preferably the alkali and alkaline earth component is well dispersed throughout the catalytic composite. The alkali or alkaline earth component will preferably comprise between 0.7 and 1.5 wt. %, or between 0.85 to 1.1 wt. %, calculated on an elemental basis of the final catalytic composite.

The alkali or alkaline earth component may be incorporated in the catalytic composite in any suitable manner such as, for example, by coprecipitation or cogelation, by ion exchange or impregnation, or by like procedures either before, while, or after other catalytic components are incorporated. A preferred method of incorporating the alkali component is to impregnate the carrier material with a solution of potassium hydroxide.

The third component of the catalyst of the present invention is a modifier metal component selected from the group consisting of tin, germanium, lead, indium, gallium, thallium, and mixtures thereof. The effective amount of the third modifier metal component is preferably uniformly impregnated. Generally, the catalyst will comprise from about 0.01 to about 10 wt. % of the third modifier metal component calculated on an elemental basis on the weight of the final composite. Preferably, the catalyst will comprise from about 0.1 to about 5 wt. % of the third modifier metal component. The third modifier metal component of the present invention preferably is tin. Some or all of the tin component may be present in the catalyst in an oxidation state above that of the elemental metal. This component may exist within the composite as a compound such as the oxide, sulfide, halide, oxychloride, aluminate, etc., or in combination with the carrier material or other ingredients of the composite. Preferably, the tin component is used in an amount sufficient to result in the final catalytic composite containing, on an elemental basis, about 0.01 to about 10 wt. % tin, with best results typically obtained with about 0.1 to about 5 wt. % tin.

The third component of the catalyst may be composited with the support in any sequence. Thus, the first or second component may be impregnated on the support followed by sequential surface or uniform impregnation of the third component. Alternatively, the third component may be surface or uniformly impregnated on the support followed by impregnation of the other catalytic component.

The catalytic composite of this invention may also contain a halogen component. The halogen component may be fluorine, chlorine, bromine, or iodine, or mixtures thereof. Chlorine is the preferred halogen components. The halogen component is generally present in a combined state with the porous carrier material and alkali component. Preferably, the halogen component is well dispersed throughout the catalytic composite. The halogen component may comprise from more than 0.01 wt. % to about 15 wt. %, calculated on an elemental basis, of the final catalytic composite.

The halogen component may be incorporated in the catalytic composite in any suitable manner, either during the preparation of the carrier material or before, while, or after other catalytic components are incorporated. For example, the alumina sol utilized to form the preferred aluminum carrier material may contain halogen and thus contribute at least some portion of the halogen content in the final catalyst composite. Also, the halogen component or a portion thereof may be added to the catalyst composite during the incorporation of the carrier material with other catalyst components, for example, by using chloroplatinic acid to impregnate the platinum component. The halogen component or a portion thereof may also be added to the catalyst composite by contacting the catalyst with the halogen or a compound or solution containing the halogen before or after other catalyst components are incorporated with the carrier material. Suitable compounds containing the halogen include acids containing the halogen, for example, hydrochloric acid. Or, the halogen component or a portion thereof may be incorporated by contacting the catalyst with a compound or solution containing the halogen in a subsequent catalyst regeneration.

In regeneration, carbon deposited on the catalyst as coke during use of the catalyst in a hydrocarbon conversion process is burned off and the catalyst and the platinum group component on the catalyst is redistributed to provide a regenerated catalyst with performance characteristics much like the fresh catalyst. The halogen component may be added during the carbon burn step or during the platinum group component redistribution step, for example, by contacting the catalyst with a hydrogen chloride gas. Also, the halogen component may be added to the catalyst composite by adding the halogen or a compound or solution containing the halogen, such as propylene dichloride, for example, to the hydrocarbon feed stream or to the recycle gas during operation of the hydrocarbon conversion process. The halogen may also be added as chlorine gas ($Cl_2$).

The carrier material of the present invention is alumina having the characteristics discussed above. The alumina carrier material may be prepared in any suitable manner from synthetic or naturally occurring raw materials. The carrier may be formed in any desired shape such as spheres, pills, cakes, extrudates, powders, granules, etc., and it may be utilized in any particle size. A preferred shape of alumina is the sphere. Additionally, the carrier material can be mono-modal, bi-modal, or a mixture thereof.

To make alumina spheres, aluminum metal is converted into an alumina sol by reacting it with a suitable peptizing agent and water, and then dropping a mixture of the sol into an oil bath to form spherical particles of the alumina gel. It is also an aspect of this invention that the third modifier metal component may be added to the alumina sol before it is reacted with a peptizing agent and dropped into the hot oil bath. Other shapes of the alumina carrier material may also be prepared by conventional methods. After the alumina particles optionally containing the co-formed third component are shaped, they are dried and calcined.

It is preferable that the final calcination step be at conditions sufficient to convert the alumina into theta-alumina which conforms to the desired characteristics of the alumina base of the instant catalyst. Such conditions would include a calcination temperature closely controlled between 950° and 1100° C. and preferably from 975° to 1050° C.

It is preferred that the alumina component is essentially theta-alumina. By "essentially theta-alumina", it is meant that at least 75% of the alumina crystallites are theta-alumina crystallites. The remaining crystallites of alumina will likely be in the form of gamma-alumina. However, other forms of alumina crystallites known in the art may also be present. It is most preferred if the essentially theta-alumina component comprises at least 90% crystallites of theta-alumina.

As explained, the theta-alumina form of crystalline alumina is produced from the amorphous alumina precursor by closely controlling the maximum calcination temperature experienced by the catalyst support. Calcination temperatures ranging from 800° to 950° C. are known to produce alumina comprising essentially crystallites of gamma-alumina. Calcination temperatures of 1100° C. and above are known to promote the formation of alpha-alumina crystallites while temperatures of from 950° to 1100° C. and especially from 975° to 1050° C. promote the formation of theta-alumina crystallites.

After the catalyst components have been combined with the desired alumina support, the resulting catalyst composite will generally be dried at a temperature of from about 100° to about 320° C. for a period of typically about 1 to 24 hours or more and thereafter calcined at a temperature of about 320° to about 600° C. for a period of about 0.5 to about 10 or more hours. Typically, chlorine-containing compounds are added to air to prevent sintering of catalyst metal components. This final calcination typically does not affect the alumina crystallites or ABD. However, the high temperature calcination of the support may be accomplished at this point if desired. Finally, the calcined catalyst composite is typically subjected to a reduction step before use in the hydrocarbon conversion process. This reduction step is effected at a temperature of about 230° to about 650° C. for a period of about 0.5 to about 10 or more hours in a reducing environment, preferably dry hydrogen, the temperature and time being selected to be sufficient to reduce substantially all of the platinum group component to the elemental metallic state.

According to one or more embodiments, the catalyst composition is used in a hydrocarbon conversion process, such as dehydrogenation. In the preferred process, dehydrogenatable hydrocarbons are contacted with the catalytic composition of the present invention in a dehydrogenation zone maintained at dehydrogenation conditions. This contacting may be accomplished in a fixed catalyst bed system, a moving catalyst bed system, a fluidized bed system, etc., or in a batch-type operation. A fixed bed system is preferred in one preferred embodiment. In this fixed bed system, the hydrocarbon feed stream is preheated to the desired reaction temperature and then passed into the dehydrogenation zone containing a fixed bed of the catalyst. The dehydrogenation zone may itself comprise one or more separate reaction zones with heating means therebetween to ensure that the desired reaction temperature can be maintained at the entrance to each reaction zone. The hydrocarbon may be contacted with the catalyst bed in either upward, downward, or radial flow fashion. Radial flow of the hydrocarbon through the catalyst bed is preferred for commercial scale reactors. The hydrocarbon may be in the liquid phase, a mixed vapor-liquid phase, or the vapor phase when it contacts the catalyst.

Hydrocarbons which may be dehydrogenated include dehydrogenatable hydrocarbons having from 2 to 30 or more carbon atoms including paraffins, alkylaromatics, naphthenes, and olefins. One group of hydrocarbons which can be dehydrogenated with the catalyst is the group of normal paraffins having from 2 to 30 or more carbon atoms. The catalyst is particularly useful for dehydrogenating paraffins having from 2 to 15 or more carbon atoms to the corresponding monoolefins or for dehydrogenating monoolefins having from 3 to 15 or more carbon atoms to the corresponding diolefins. The catalyst is especially useful in the dehydrogenation of C2-C6 paraffins, primarily propane and butanes, to monoolefins.

Dehydrogenation conditions include a temperature of from about 400° to about 900° C., a pressure of from about 0.01 to 10 atmospheres absolute, and a liquid hourly space velocity (LHSV) of from about 0.1 to 100 $hr^{-1}$. Generally, for normal paraffins, the lower the molecular weight, the higher the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen, and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions, or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while, or after being passed to the dehydrogenation zone. The diluent material may be hydrogen, steam, methane, ethane, carbon dioxide, nitrogen, argon, and the like or a mixture thereof. Hydrogen and steam are the preferred diluents. Ordinarily, when hydrogen or steam is utilized as the diluent, it is utilized in amounts sufficient to ensure a diluent-to-hydrocarbon mole ratio of about 0.1:1 to about 40:1, with best results being obtained when the mole ratio range is about 0.4:1 to about 10:1. The diluent stream passed to the dehydrogenation zone will typically be recycled diluent separated from the effluent from the dehydrogenation zone in a separation zone.

A combination of diluents, such as steam with hydrogen, may be employed. When hydrogen is the primary diluent water or a material which decomposes at dehydrogenation conditions to form water such as an alcohol, aldehyde, ether, or ketone, for example, may be added to the dehydrogenation zone, either continuously or intermittently, in an amount to provide, calculated on the basis of equivalent water, about 1 to about 20,000 weight ppm of the hydrocarbon feed stream. About 1 to about 10,000 weight ppm of water addition gives best results when dehydrogenating paraffins have from 6 to 30 or more carbon atoms.

To be commercially successful, a dehydrogenation catalyst should exhibit three characteristics, namely, high activity, high selectivity, and good stability. Activity is a measure of the catalyst's ability to convert reactants into products at a specific set of reaction conditions, that is, at a specified temperature, pressure, contact time, and concentration of diluent such as hydrogen, if any. For dehydrogenation catalyst activity, the conversion or disappearance of paraffins in percent relative to the amount of paraffins in the feedstock is measured. Selectivity is a measure of the catalyst's ability to convert reactants into the desired product or products relative to the amount of reactants converted. For catalyst selectivity, the amount of olefins in the product, in mole percent, relative to the total moles of the paraffins converted is measured. Stability is a measure of the rate of change with time on stream of the activity and selectivity parameters—the smaller rates implying the more stable catalysts.

The dehydrogenation of hydrocarbons is an endothermic process. In a system employing a dehydrogenation catalyst only, it is typically necessary to add superheated steam at various points in the process or to intermittently remove and reheat the reaction stream between catalyst beds. Some processes have been developed which utilize a two-catalyst system with distinct beds or reactors of dehydrogenation or selective oxidation catalysts. The purpose of the selective oxidation catalysts is to selectively oxidize the hydrogen produced as a result of the dehydrogenation reaction with oxygen that had been added to the oxidation zone to generate heat internally in the process. The heat generated typically is sufficient to cause the reaction mixture to reach desired dehydrogenation temperatures for the next dehydrogenation step. The instant process may be accomplished in this previously mentioned system. If such a process is employed, the instant catalyst would comprise at least the dehydrogenation catalyst with another specific catalyst being used to accomplish the oxidation reaction.

The selective oxidation step, if utilized, uses the hydrogen which has been produced in the dehydrogenation step of the process to supply heat to the next dehydrogenation reaction section. To accomplish this, an oxygen-containing gas is first introduced into the reactor, preferably at a point adjacent to the selective oxidative catalyst section. The oxygen in the oxygen-containing gas is necessary to oxidize the hydrogen contained in the reaction stream. Examples of oxygen-containing gases which may be utilized to effect the selective oxidation of the hydrogen which is present will include air, oxygen, or air or oxygen diluted with other gases such as steam, carbon dioxide and inert gases such as nitrogen, argon, helium, etc. The amount of oxygen which is introduced to contact the process stream may range from about 0.01:1 to about 2:1 moles of oxygen per mole of hydrogen contained in the process stream at the point where oxygen is added to the process stream. In the selective oxidation reaction, the process stream which comprises unreacted dehydrogenatable hydrocarbon, dehydrogenated hydrocarbon, and hydrogen is reacted with oxygen in the presence of the selective steam oxidation/dehydrogenation catalyst whereby hydrogen is selectively oxidized to produce water and heat energy with very little of the oxygen reacting with the hydrocarbons.

The selective steam oxidation/dehydrogenation catalyst may be one that is useful for the selective oxidation of hydrogen in the presence of hydrocarbons. An example of such a catalyst is disclosed in U.S. Pat. No. 4,418,237. Alternatively, the catalyst used for the selective oxidation step may be identical to the catalyst utilized for the dehydrogenation step. Such catalysts or processes for their use are disclosed in U.S. Pat. Nos. 4,613,715 and 3,670,044.

The oxygen-containing reactant may be added to the instant process in various ways such as by admixing oxygen with a relatively cool hydrocarbon feed stream or with the steam diluent, or it may be added directly to the reactor independently of the feed hydrocarbons or the steam diluent. In addition, the oxygen-containing reactant can be added at one or more points in the reactor in such a fashion as to minimize local concentrations of oxygen relative to hydrogen in order to distribute the beneficial temperature rise produced by the selective hydrogen oxidation over the entire length of the reaction zone. The use of multiple injection points minimizes the opportunity for local build-up of the concentration of oxygen relative to the amount of hydrogen, thereby minimizing the opportunity for undesired reaction of the oxygen-containing gas with either feed or product hydrocarbons.

The following example is introduced to further describe the catalyst and process of the invention. This example is intended as an illustrative embodiment and should not be considered to restrict the otherwise broad interpretation of the invention as set forth in the claims appended hereto.

EXAMPLES

Propane Dehydrogenation

In order to demonstrate the advantages to be achieved by the present invention, a catalyst of this invention and three state-of-the-art catalysts were prepared.

The first prior art catalyst (Catalyst A) contained a median pore diameter of 1.6 mm with an ABD of 0.62 g/cc. The second prior art catalyst (Catalyst B) contained a median pore diameter of 1.8 mm with an ABD of 0.63 g/cc. The third prior art catalyst (Catalyst C) contained a median pore diameter of 1.8 mm and ABD of 0.62 g/cc. The catalyst according to the present invention (Catalyst D) contained a median pore diameter of 1.8 mm and an ABD of 0.56 g/cc. All of these catalysts had the same amount (approximately) of platinum, tin, and potassium on a volumetric level. The properties of the catalysts are presented in Table 1 for comparison and the results of the testing are shown in FIG. 1.

TABLE 1

|  | Catalyst A | Catalyst B | Catalyst C | Catalyst D |
|---|---|---|---|---|
| ABD (g/cc) | 0.62 | 0.63 | 0.62 | 0.56 |
| Median Diameter (mm) | 1.6 | 1.8 | 1.8 | 1.8 |
| BET Surface Area (m2/g) | 86 | 81 | 82 | 85 |
| Total Hg Intrusion volume (cc/g) | 0.79 | 0.74 | 0.77 | 0.89 |
| Median Pore Diameter (Hg) (Å) | 239 | 237 | 113 | 277 |
| Porosity | 79.7 | 70 | 80.9 | 82.6 |
| Diffusivity | 1.67E−6 (avg.) | n/a | 1.46E−6 | 2.13E−6 |
| Maximum Propane Conversion | 16.7 | 15.9 | 16.6 | 17.5 |
| Propane Conversion Slope | −0.20 | −0.25 | −0.25 | −0.21 |

Figure 2:
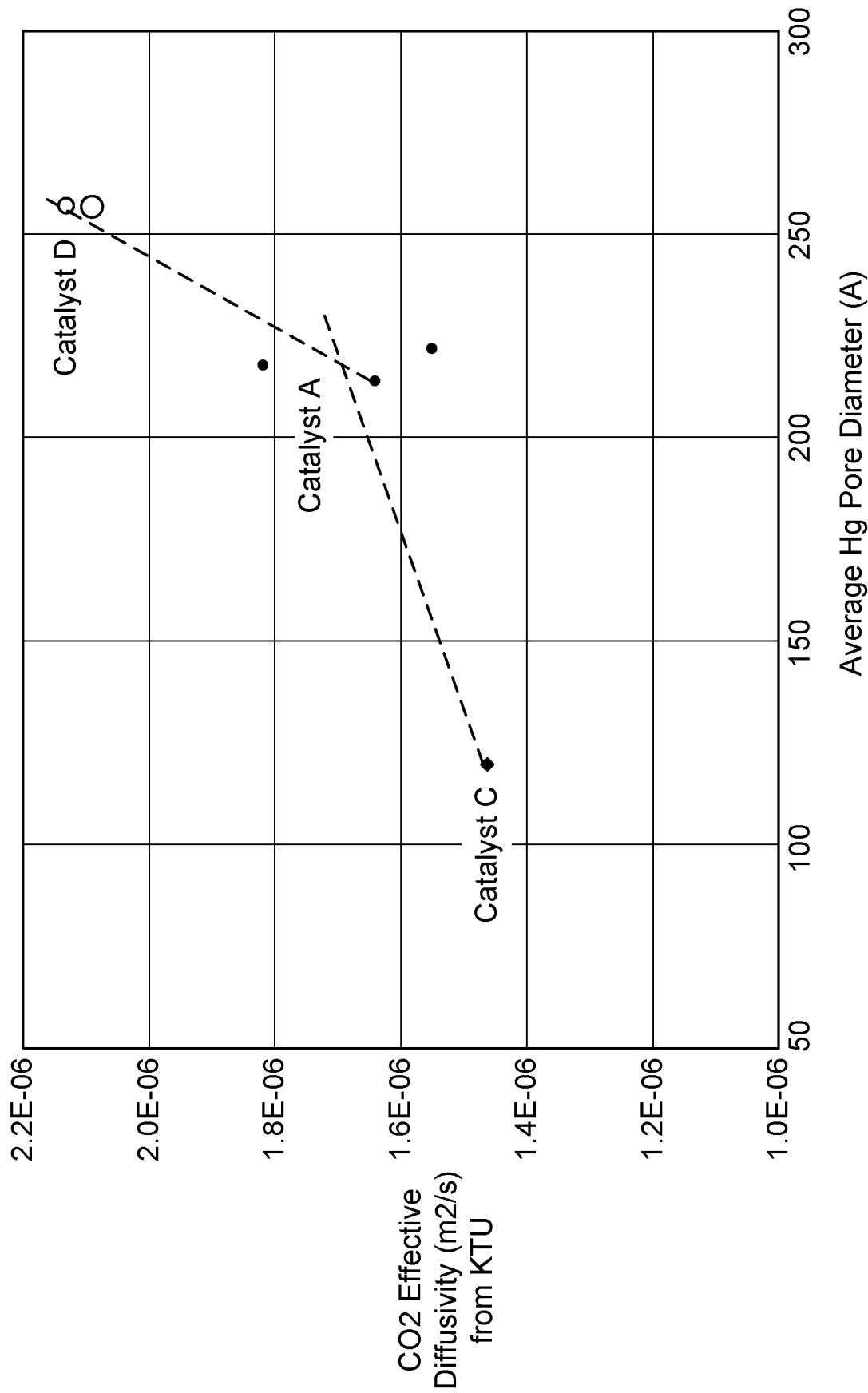
FIG. 2 shows a graph plotting measured carbon dioxide effective diffusivities versus average pore diameter for a catalyst according to the present invention compared with two prior art catalysts.

The diffusivity was measured at 10° C. with a Kinetic Testing Unit (KTU) using carbon dioxide as the probe molecule. The values obtained from the KTU are shown in FIG. 2.

Each catalyst (approximately 15 cc) was tested in a pilot plant to dehydrogenate propane to produce propylene for 20 hours on stream (HOS). The operating conditions of each pilot plant test included a feed with 77% propane and 23% (by weight) propylene, and a hydrogen to feed ratio of 0.7, a liquid hourly space velocity (LHSV) of 30 $hr^{-1}$, a pressure of 135 kPa (5 psig), a feed temperature of 650° C. (1202° F.), and 70 ppm of hydrogen sulfide. The results of the tests are reflected in FIG. 1 demonstrating the propane conversion plotted against the total hours on stream.

From FIG. 1, it can be seen that the catalyst of the present invention (Catalyst D) demonstrates the highest initial maximum activity and maintains a higher propane conversion to 20 hours on stream than the prior art catalysts at the same operating conditions.

Spent Catalyst Regeneration (Coke Burn)

Catalysts A, C, and D from the foregoing propane dehydrogenation were analyzed after being taken off stream. The spent catalyst particles were analyzed via thermogravimetric analysis (TGA).

For the TGA, 50 mg (approximately 14-20 catalyst particles) were pretreated to desorb volatile substances at 550° C. in nitrogen gas. After the pretreatment, two temperature measurements were used. The catalyst particles were either cooled to 480° C. or held at 550° C. and 1% oxygen gas was added to the flowing nitrogen gas to burn off the coke that had been formed on the catalyst. The TGA data was processed using the shell progressive diffusion model to calculate the coke burn time and the Oxygen Effective Diffusivities. The results of the 480° C. TGA processed data are shown in FIG. 3 and the calculated Oxygen Diffusivities are shown in the below TABLE 2 and FIG. 4.

TABLE 2

|  | Burn Temperature | Median Pore Diameter (Hg), (Å) | Oxygen Diffusivity (m²/s) |
|---|---|---|---|
| Catalyst D | 480° C. | 257 | 2.6E−7 |
| Catalyst A | 480° C. | 222 | 1.42E−7 |
| Catalyst A | 480° C. | 222 | 1.469E−7 |
| Catalyst A | 480° C. | 222 | 1.845E−7 |
| Catalyst A | 480° C. | 222 | 1.516E−7 |
| Catalyst C | 480° C. | 115 | 7.471E−8 |
| Catalyst C | 480° C. | 115 | 1.264E−7 |
| Catalyst D | 550° C. | 257 | 8.376E−7 |
| Catalyst A | 550° C. | 222 | 5.447E−7 |
| Catalyst A | 550° C. | 222 | 5.588E−7 |
| Catalyst A | 550° C. | 222 | 5.578E−7 |
| Catalyst C | 550° C. | 115 | 2.079E−7 |
| Catalyst C | 550° C. | 115 | 3.152E−7 |

Figure 3:
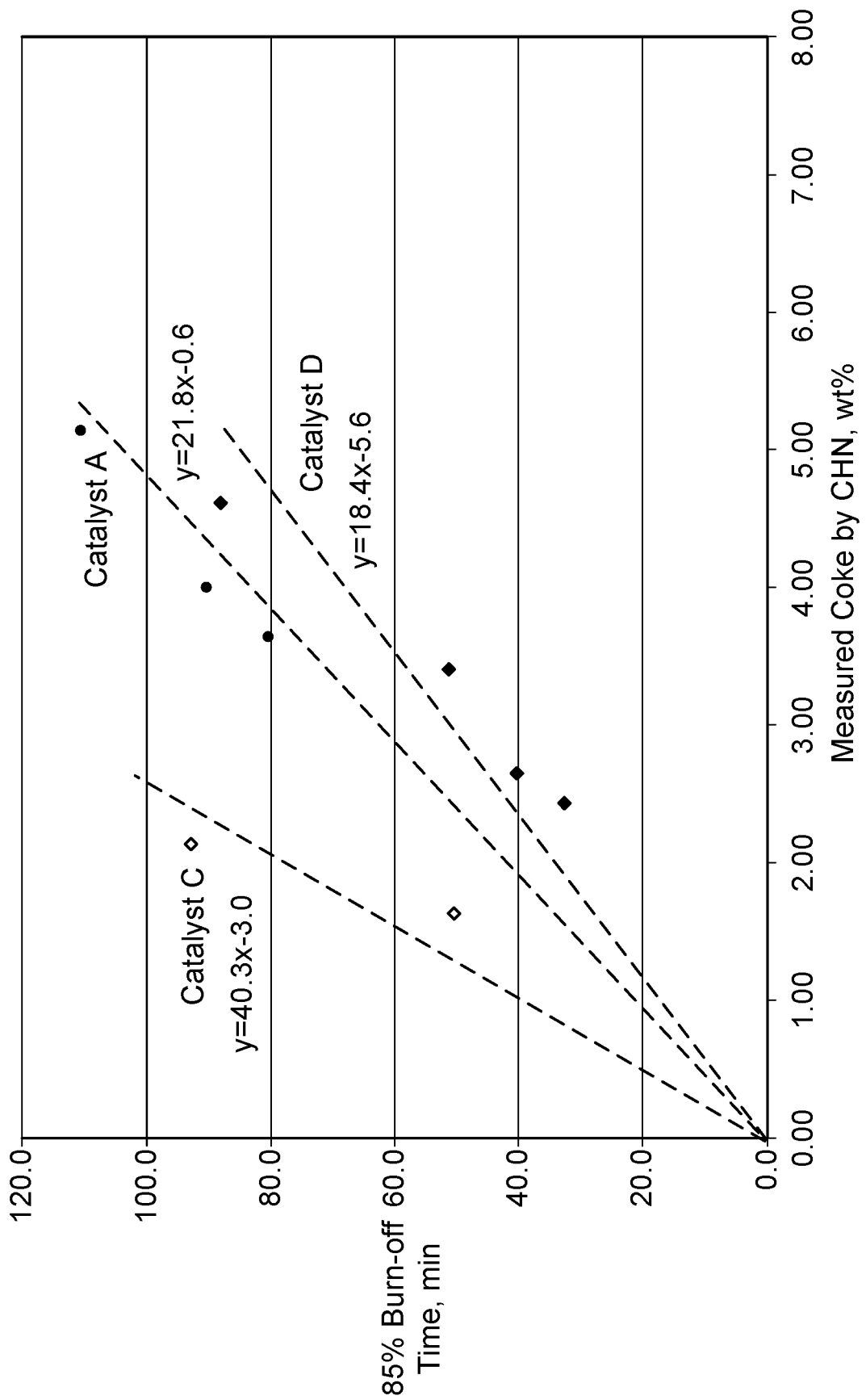
FIG. 3 shows a graph plotting time to 85% carbon burn off versus measured coke amounts for the catalysts in FIG. 2; and, FIG. 4 shows a graph plotting calculated oxygen effective diffusivities versus average pore diameter for a catalyst according to the present invention compared with two prior art catalysts.
Figure 4:
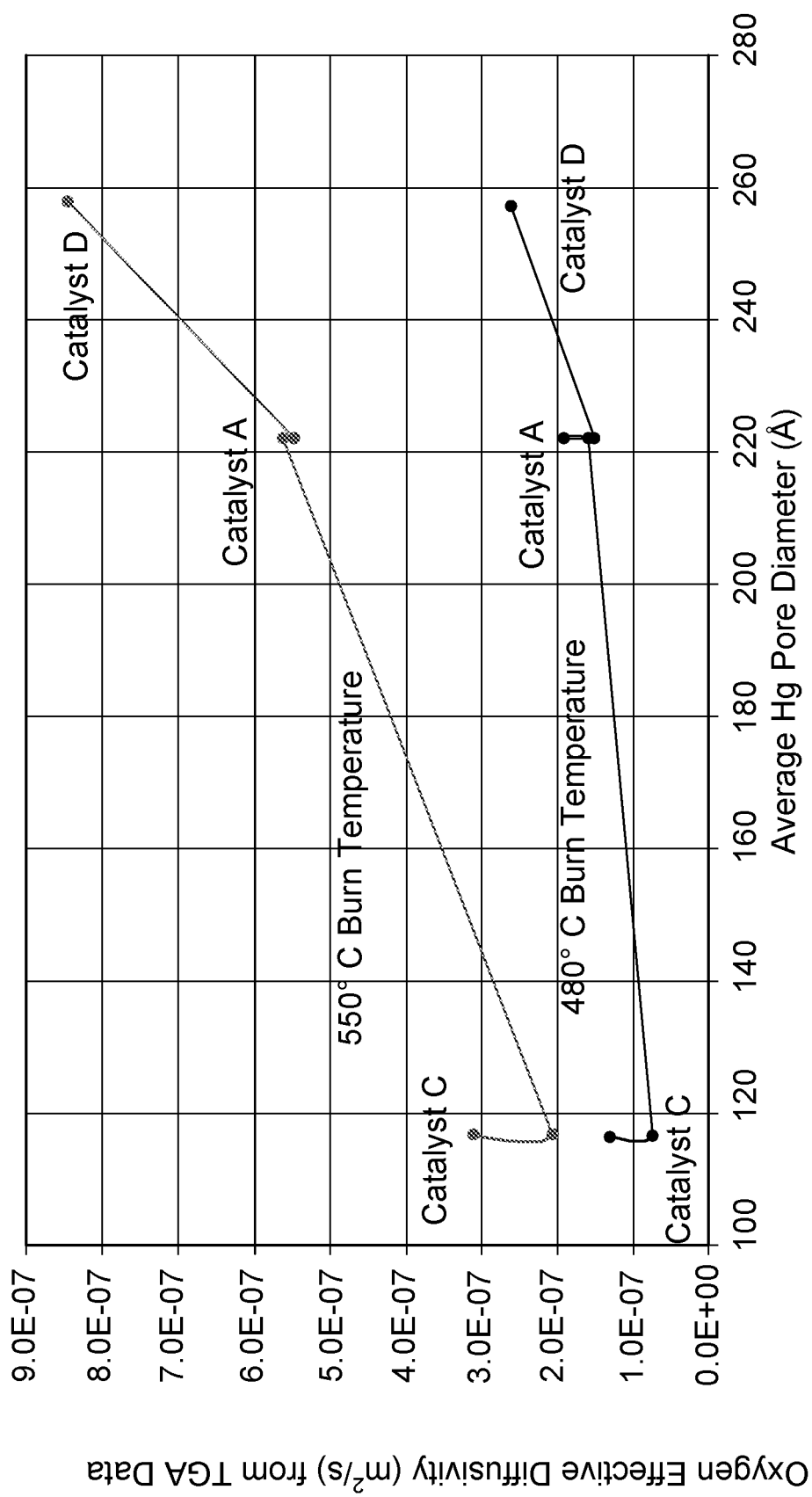

From FIGS. 3 and 4, it can be seen that the catalyst of the present invention (Catalyst D) demonstrates the shortest coke burn time and the highest oxygen effective diffusivities. This is surprising and unexpected given the large particle diameter and long diffusion paths. Indeed, initial calculations indicated that Catalyst D would have 27% longer burn time. However, as shown in FIG. 3, Catalyst D actually had an 18% shorter burn off time compared to Catalyst A, and at least a 50% shorter burn time compared to Catalyst C. Thus, not only does the present catalytic composition provide superior results for the selective hydrocarbon conversion process, it also has superior and unexpected results associated with regeneration.

Any of the above lines, conduits, units, devices, vessels, surrounding environments, zones or similar may be equipped with one or more monitoring components including sensors, measurement devices, data capture devices or data transmission devices. Signals, process or status measurements, and data from monitoring components may be used to monitor conditions in, around, and on process equipment. Signals, measurements, and/or data generated or recorded by monitoring components may be collected, processed, and/or transmitted through one or more networks or connections that may be private or public, general or specific, direct or indirect, wired or wireless, encrypted or not encrypted, and/or combination(s) thereof; the specification is not intended to be limiting in this respect.

Signals, measurements, and/or data generated or recorded by monitoring components may be transmitted to one or more computing devices or systems. Computing devices or systems may include at least one processor and memory storing computer-readable instructions that, when executed by the at least one processor, cause the one or more computing devices to perform a process that may include one or more steps. For example, the one or more computing devices may be configured to receive, from one or more monitoring component, data related to at least one piece of equipment associated with the process. The one or more computing devices or systems may be configured to analyze the data. Based on analyzing the data, the one or more computing devices or systems may be configured to determine one or more recommended adjustments to one or more parameters of one or more processes described herein. The one or more computing devices or systems may be configured to transmit encrypted or unencrypted data that includes the one or more recommended adjustments to the one or more parameters of the one or more processes described herein.

SPECIFIC EMBODIMENTS

While the following is described in conjunction with specific embodiments, it will be understood that this description is intended to illustrate and not limit the scope of the preceding description and the appended claims.

A first embodiment of the invention is a process for reducing a time associated with regenerating a catalyst used for a selective conversion of hydrocarbons, the process comprising removing coke from a catalyst comprising a first component selected from the group consisting of Group VIII noble metals and mixtures thereof, a second component selected from the group consisting of alkali metals or alkaline-earth metals and mixtures thereof, a third component selected from the group consisting of tin, germanium, lead, indium, gallium, thallium and mixtures thereof, and wherein the time associated with regenerating the catalyst is reduced at least 10% compared to a theoretical time for regenerating the catalyst by the catalyst further comprising a support forming a catalyst particle with a median diameter between 1.6 mm and 2.5 mm and an apparent bulk density between 0.6 and 0.3 g/cc. An embodiment of the invention is one, any or all of prior embodiments in this paragraph up through the first embodiment in this paragraph wherein the apparent bulk density is between 0.6 and 0.5 g/cc. An embodiment of the invention is one, any or all of prior embodiments in this paragraph up through the first embodiment in this paragraph wherein the median diameter is between 1.8 mm and 2.2 mm. An embodiment of the invention is one, any or all of prior embodiments in this paragraph up through the first embodiment in this paragraph wherein the median diameter is between 1.8 mm and 2.2 mm. An embodiment of the invention is one, any or all of prior embodiments in this paragraph up through the first embodiment in this paragraph wherein the apparent bulk density is between 0.57 to 0.52 g/cc. An embodiment of the invention is one, any or all of prior embodiments in this paragraph up through the first embodiment in this paragraph wherein the median diameter is 1.8 mm. An embodiment of the invention is one, any or all of prior embodiments in this paragraph up through the first embodiment in this paragraph wherein the apparent bulk density is 0.57 g/cc. An embodiment of the invention is one, any or all of prior embodiments in this paragraph up through the first embodiment in this paragraph wherein the catalyst has mono-modal porous distribution. An embodiment of the invention is one, any or all of prior embodiments in this paragraph up through the first embodiment in this paragraph wherein the catalyst has bi-modal porous distribution. An embodiment of the invention is one, any or all of prior embodiments in this paragraph up through the first embodiment in this paragraph wherein, the first component is platinum, the second component is potassium, and the third component is tin. An embodiment of the invention is one, any or all of prior embodiments in this paragraph up through the first embodiment in this paragraph wherein the support is selected from the group consisting of silica, alumina, silica-alumina, a zeolite, a non-zeolitic molecular sieve, titania, zirconia and mixtures thereof. An embodiment of the invention is one, any or all of prior embodiments in this paragraph up through the first embodiment in this paragraph wherein the support is selected from the group consisting of theta-alumina, gamma-alumina, eta-alumina, delta-alumina, and mixtures thereof. An embodiment of the invention is one, any or all of prior embodiments in this paragraph up through the first embodiment in this paragraph wherein the noble metal is in an amount between 0.01 wt. % and 5 wt. % based on the total weight. An embodiment of the invention is one, any or all of prior embodiments in this paragraph up through the first embodiment in this paragraph wherein the second component is in an amount between 0.7 wt. % and 1.5 wt. % based on the total weight. An embodiment of the invention is one, any or all of prior embodiments in this paragraph up through the first embodiment in this paragraph wherein the third component is in an amount between 0.01 wt. % and 5 wt. % based on the total weight. An embodiment of the invention is one, any or all of prior embodiments in this paragraph up through the first embodiment in this paragraph wherein the catalyst particle is spherical. An embodiment of the invention is one, any or all of prior embodiments in this paragraph up through the first embodiment in this paragraph wherein the catalyst has an oxygen effective diffusivity at 480° C. of at least $1.5 \times 10^{-7}$ $m_2/s$. An embodiment of the invention is one, any or all of prior embodiments in this paragraph up through the first embodiment in this paragraph wherein the catalyst particle has an effective carbon dioxide diffusivity at 10° C. of at least $1.6 \times 10^{-6}$ $m^2/sec$.

A second embodiment of the invention is a process for regenerating a catalyst used for a selective conversion of hydrocarbons, the process comprising removing coke from a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a catalyst particle with a median diameter between 1.6 mm and 2.5 mm and an apparent bulk density between 0.6 and 0.3 g/cc, and wherein a time associated with removing coke from the catalytic composite is lower than a calculated time to remove coke from the catalytic composite.

A third embodiment of the invention is a catalyst for a selective conversion of hydrocarbons, the catalyst comprising a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof; and a support forming a spherical catalyst particle with a median diameter between 1.6 mm and 2.5 mm and an apparent bulk density between 0.6 and 0.3 g/cc. An embodiment of the invention is one, any or all of prior embodiments in this paragraph up through the third embodiment in this paragraph wherein the apparent bulk density is between 0.6 and 0.5 g/cc. An embodiment of the invention is one, any or all of prior embodiments in this paragraph up through the third embodiment in this paragraph wherein the median diameter is between 1.8 mm and 2.2 mm. An embodiment of the invention is one, any or all of prior embodiments in this paragraph up through the third embodiment in this paragraph wherein the median diameter is between 1.8 mm and 2.2 mm. An embodiment of the invention is one, any or all of prior embodiments in this paragraph up through the third embodiment in this paragraph wherein the apparent bulk density is between 0.57 to 0.52 g/cc. An embodiment of the invention is one, any or all of prior embodiments in this paragraph up through the third embodiment in this paragraph wherein the median diameter is 1.8 mm. An embodiment of the invention is one, any or all of prior embodiments in this paragraph up through the third embodiment in this paragraph wherein the apparent bulk density is 0.57 g/cc. An embodiment of the invention is one, any or all of prior embodiments in this paragraph up through the third embodiment in this paragraph wherein the catalyst has mono-modal porous distribution. An embodiment of the invention is one, any or all of prior embodiments in this paragraph up through the third embodiment in this paragraph wherein, the first component is platinum, the second component is potassium, and the third component is tin. An embodiment of the invention is one, any or all of prior embodiments in this paragraph up through the third embodiment in this paragraph wherein the support is selected from the group consisting of silica, alumina, silica-alumina, a zeolite, a non-zeolitic molecular sieve, titania, zirconia and mixtures thereof. An embodiment of the invention is one, any or all of prior embodiments in this paragraph up through the third embodiment in this paragraph wherein the support is selected from the group consisting of theta-alumina, gamma-alumina, eta-alumina, delta-alumina, and mixtures thereof. An embodiment of the invention is one, any or all of prior embodiments in this paragraph up through the third embodiment in this paragraph wherein the catalyst has an effective carbon dioxide diffusivity at 10° C. of at least $1.6 \times 10^{-6}$ m$^2$/sec. An embodiment of the invention is one, any or all of prior embodiments in this paragraph up through the third embodiment in this paragraph wherein the noble metal is in an amount between 0.01 wt. % and 5 wt. % based on the total weight. An embodiment of the invention is one, any or all of prior embodiments in this paragraph up through the third embodiment in this paragraph wherein the second component is in an amount between 0.7 wt. % and 1.5 wt. % based on the total weight. An embodiment of the invention is one, any or all of prior embodiments in this paragraph up through the third embodiment in this paragraph wherein the third component is in an amount between 0.01 wt. % and 5 wt. % based on the total weight.

A fourth embodiment of the invention is a process for the selective conversion of hydrocarbons, the process comprising contacting a hydrocarbon at selective conversion conditions with a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a spherical catalyst particle with a median diameter between 1.6 mm and 2.5 mm and an apparent bulk density between 0.6 and 0.3 g/cc. An embodiment of the invention is one, any or all of prior embodiments in this paragraph up through the fourth embodiment in this paragraph wherein the hydrocarbon comprises propane, and wherein the selective conversion comprises dehydrogenation. An embodiment of the invention is one, any or all of prior embodiments in this paragraph up through the fourth embodiment in this paragraph wherein the median diameter of the catalyst is 1.8 mm and wherein the apparent bulk density is 0.57 g/cc.

A fifth embodiment of the invention is a process for the regeneration a catalyst used for a selective conversion of hydrocarbons, the process comprising removing coke from a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a spherical catalyst particle with a median diameter between 1.6 mm and 2.5 mm and an apparent bulk density between 0.6 and 0.3 g/cc. An embodiment of the invention is one, any or all of prior embodiments in this paragraph up through the fifth embodiment in this paragraph wherein the median diameter of the catalyst is 1.8 mm and wherein the apparent bulk density is 0.57 g/cc.

A sixth embodiment of the invention is a process for a selective conversion of hydrocarbons, the catalyst comprising a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof; and a support forming a spherical catalyst particle with an average pore diameter between 200 to 350 Angstroms, a porosity of at least 75% and an apparent bulk density between 0.60 and 0.3 g/cc. An embodiment of the invention is one, any or all of prior embodiments in this paragraph up through the sixth embodiment in this paragraph wherein the apparent bulk density is between 0.60 and 0.5 g/cc. An embodiment of the invention is one, any or all of prior embodiments in this paragraph up through the fifth embodiment in this paragraph wherein the apparent bulk density is between 0.57 to 0.52 g/cc. An embodiment of the invention is one, any or all of prior embodiments in this paragraph up through the sixth embodiment in this paragraph wherein the wherein the apparent bulk density is 0.57 g/cc. An embodiment of the invention is one, any or all of prior embodiments in this paragraph up through the sixth embodiment in this paragraph wherein the apparent bulk density is between 0.57 to 0.52 g/cc. An embodiment of the invention is one, any or all of prior embodiments in this paragraph up through the sixth embodiment in this paragraph wherein the average pore diameter is between 240 to 280 Angstroms. An embodiment of the invention is one, any or all of prior embodiments in this paragraph up through the sixth embodiment in this paragraph wherein the catalyst has mono-modal porous distribution. An embodiment of the invention is one, any or all of prior embodiments in this paragraph up through the sixth embodiment in this paragraph wherein, the first component is platinum, the second component is potassium, and the third component is tin. An embodiment of the invention is one, any or all of prior embodiments in this paragraph up through the sixth embodiment in this paragraph wherein the support is selected from the group consisting of silica, alumina, silica-alumina, a zeolite, a non-zeolitic molecular sieve, titania, zirconia and mixtures thereof. An embodiment of the invention is one, any or all of prior embodiments in this paragraph up through the sixth embodiment in this paragraph wherein the support is selected from the group consisting of theta-alumina, gamma-alumina, eta-alumina, delta-alumina, and mixtures thereof. An embodiment of the invention is one, any or all of prior embodiments in this paragraph up through the sixth embodiment in this paragraph wherein the catalyst has an oxygen effective diffusivity at 480° C. of at least $1.5 \times 10^{-7}$ m$^2$/s. An embodiment of the invention is one, any or all of prior embodiments in this paragraph up through the sixth embodiment in this paragraph wherein the noble metal is in an amount between 0.01 wt. % and 5 wt. % based on the total weight. An embodiment of the invention is one, any or all of prior embodiments in this paragraph up through the sixth embodiment in this paragraph wherein the second component is in an amount between 0.7 wt. % and 1.5 wt. % based on the total weight. An embodiment of the invention is one, any or all of prior embodiments in this paragraph up through the sixth embodiment in this paragraph wherein the third component is in an amount between 0.01 wt. % and 5 wt. % based on the total weight. An embodiment of the invention is one, any or all of prior embodiments in this paragraph up through the sixth embodiment in this paragraph wherein the catalyst has a median diameter between 1.8 mm and 2.2 mm.

A seventh embodiment of the invention is a process for regenerating a catalyst used for a selective conversion of hydrocarbons, the process comprising removing coke from a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a support forming a spherical catalyst particle with an average pore diameter between 200 to 350 Angstroms, a porosity of at least 80% and an apparent bulk density between 0.60 and 0.3 g/cc. An embodiment of the invention is one, any or all of prior embodiments in this paragraph up through the seventh embodiment in this paragraph wherein the apparent bulk density is between 0.60 and 0.5 g/cc. An embodiment of the invention is one, any or all of prior embodiments in this paragraph up through the seventh embodiment in this paragraph wherein the average pore diameter is between 240 to 280 Angstroms.

An eighth embodiment of the invention is a process for the selective conversion of hydrocarbons, the process comprising contacting a hydrocarbon at selective conversion conditions with a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a spherical catalyst particle with an average pore diameter between 200 to 350 Angstroms, a porosity of at least 80% and an apparent bulk density between 0.60 and 0.3 g/cc. An embodiment of the invention is one, any or all of prior embodiments in this paragraph up through the eighth embodiment in this paragraph wherein the apparent bulk density is between 0.60 and 0.5 g/cc.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A process for reducing a time associated with regenerating a catalyst used for a selective conversion of hydrocarbons, the process comprising:
   removing coke from a catalyst comprising a first component selected from the group consisting of Group VIII noble metals and mixtures thereof, a second component selected from the group consisting of alkali metals or alkaline-earth metals and mixtures thereof, a third component selected from the group consisting of tin, germanium, lead, indium, gallium, thallium and mixtures thereof, and wherein the time associated with regenerating the catalyst is reduced at least 10% compared to a theoretical time for regenerating the catalyst by the catalyst further comprising a support forming a catalyst particle with a median diameter between 1.6 mm and 2.5 mm and an apparent bulk density between 0.6 and 0.3 g/cc.

2. The process of claim 1 wherein the apparent bulk density is between 0.6 and 0.5 g/cc.

3. The process of claim 2 wherein the median diameter is between 1.8 mm and 2.2 mm.

4. The process of claim 1 wherein the median diameter is between 1.8 mm and 2.2 mm.

5. The process of claim 4 wherein the apparent bulk density is between 0.57 to 0.52 g/cc.

6. The process of claim 1 wherein the median diameter is 1.8 mm.

7. The process of claim 6 wherein the apparent bulk density is 0.57 g/cc.

8. The process of claim 1 wherein the catalyst has mono-modal porous distribution.

9. The process of claim 1 wherein the catalyst has bi-modal porous distribution.

10. The process of claim 1 wherein, the first component is platinum, the second component is potassium, and the third component is tin.

11. The process of claim 1 wherein the support is selected from the group consisting of silica, alumina, silica-alumina, a zeolite, a non-zeolitic molecular sieve, titania, zirconia and mixtures thereof.

12. The process of claim 11 wherein the support is selected from the group consisting of theta-alumina, gamma-alumina, eta-alumina, delta-alumina, and mixtures thereof.

13. The process of claim 1 wherein the noble metal is in an amount between 0.01 wt. % and 5 wt. % based on the total weight.

14. The process of claim 1 wherein the second component is in an amount between 0.7 wt. % and 1.5 wt. % based on the total weight.

15. The process of claim 1 wherein the third component is in an amount between 0.01 wt. % and 5 wt. % based on the total weight.

16. The process of claim 1 wherein the catalyst particle is spherical.

17. The process of claim 1 wherein the catalyst has an oxygen effective diffusivity at 480° C. of at least $1.5 \times 10^{-7}$ m$^2$/s.

18. The process of claim 1 wherein the catalyst particle has an effective carbon dioxide diffusivity at 10° C. of at least $1.6 \times 10^{-6}$ m$^2$/sec.

19. A process for regenerating a catalyst used for a selective conversion of hydrocarbons, the process comprising:

removing coke from a catalytic composite a first component selected from the group consisting of Group VIII noble metals and mixtures thereof, a second component selected from the group consisting of alkali metals or alkaline-earth metals and mixtures thereof, and a third component selected from the group consisting of tin, germanium, lead, indium, gallium, thallium and mixtures thereof and a support forming a catalyst particle with a median diameter between 1.6 mm and 2.5 mm and an apparent bulk density between 0.6 and 0.3 g/cc, and wherein a time associated with removing coke from the catalytic composite is lower than a calculated time to remove coke from the catalytic composite.

20. The process of claim 19 wherein the time associated with removing coke from the catalytic composite is at least 10% lower than a calculated time to remove coke from the catalytic composite.

* * * * *